United States Patent [19]

Parker et al.

[11] 4,059,575

[45] Nov. 22, 1977

[54] PROCESS FOR THE PREPARATION OF 17(20)ENE-21-STEROID ALDEHYDES

[75] Inventors: Kathlyn A. Parker, Providence, R.I.; Raymond W. Kosley, Jr., Convent Station, N.J.

[73] Assignee: Research Corporation, New York, N.Y.

[21] Appl. No.: 679,152

[22] Filed: Apr. 22, 1976

[51] Int. Cl.$^2$ .......................... C07J 33/00; C07J 21/00
[52] U.S. Cl. .......................... 260/239.5; 260/239.55 C; 260/397.5
[58] Field of Search .................... 260/397.4, 239.55 C, 260/397.5

[56] References Cited

U.S. PATENT DOCUMENTS

| | | | |
|---|---|---|---|
| 3,094,524 | 6/1963 | Bertin et al. | 260/239.55 |
| 3,912,656 | 10/1975 | Andrews et al. | 260/397.47 |

*Primary Examiner*—Elbert L. Roberts
*Attorney, Agent, or Firm*—Behr & Woodbridge

[57] ABSTRACT

There is disclosed a process for the efficient conversion of 17-α-ethynyl 17-β- hydroxy steroids into the corresponding 17(20) αβ-unsaturated 21-steroid aldehydes. The process comprises the sequential steps of reacting the ethynyl alcohol with a diloweralkylformamide dilower-alkylacetal, suitably dimethylformamide diethylacetal, to form the corresponding 16,20 diene-21-diloweralkylamine which is then hydrolyzed to form the corresponding 17(20)-ene-21-steroid aldehyde.

18 Claims, No Drawings

PROCESS FOR THE PREPARATION OF 17(20)ENE-21-STEROID ALDEHYDES

The invention described herein was made in the course of work under a grant or award from the Department of Health, Education and Welfare.

DESCRIPTION OF THE PRIOR ART

The process of the present invention is applicable to a very closely related group of steriod aldehydes. This group comprises the 17(20)-en-21-aldehydes of 19-norpregna-1,3,5(10)-triene 3-ethers and the 3-ethylene ketals and 3-ethylene-thioketals of 3-keto pregn-4-ene.

Members of the first subgeneric category are known. For example, trans-3-methoxy-19-norpregna-1,3,5(10), 17(20) tetraen-21-al has been prepared from the same starting material by Benn, J. Org. Chem., 33, 3113 (1968). The Benn procedure differs from the present procedure in the important aspect that the formation of the intermediate propargyl acetate is required and the second step to the desired aldehyde requires prolonged heating in acetic acid in the presence of silver ion catalyst. The overall yield from the starting alcohol to the final aldehyde as reported by Benn is of the order of 63% in contrast to the 90+% yield obtained by the present procedures. Furthermore, the procedures of the present invention do not require the purification of the intermediate dieneamine although this may be done if desired. The starting material for the process of the present invention (as well as that of Benn's procedures) may be obtained by the procedures of Stavely, J. Amer. Chem. Soc., 61, 79 (1939). Other more complex and sensitive procedures for producing these aldehydes are known. It is believed, however, that none of them can be readily carried out on a commercial scale as is believed to be possible in the case of the present procedures. Reference may be had to Heusser et al., Helv. Chem. Acta. 33, 370 (1950); Smith et al., Steriods, 8, 947 (1966); Nagata and Hayase, Tetrahedron Letters, 4359 (1968) and J. Chem. Soc. (C) 1969, 460.

As stated by Benn the compounds of this category have utility as hypocholesteremic, estrogenic, antifertility, antiinflammatory, progestational, and antihypertensive agents. With respect to the other subgenus, namely, the 17-ethynyl-17- hydroxy steroids protected at the 3 position of the steriod nucleus, it may be stated that the ethylene ketal is prepared by the procedure of Barton et al.; J. Chem. Soc. 1957-62 (1959) and U.S. Pat. No. 2,288,854. The corresponding ketal aldehyde prepared by the process of the present invention does not appear to be known heretofore.

The corresponding thioketal is disclosed by Fetizon and Jurion, Chem. Commun. 382 (1972) and published German Application (OLS) No. 2704116. The material as utilized in the present invention is prepared in accordance with the procedure of Ralls and Riegel J. Amer. Chem. Soc. 76 4479 (1954).

The interaction of ethynyl carbinols and dialkyl alkanoyl amide dialkylacetals has been stuided heretofore. However, different results are obtained where the acetal is a dialkylformamide dialkylacetal or a dialkylalkanoylamide alkylacetal wherein the alkanoyl group is other than formyl. Further differences have been noted (by the inventors in unpublished work) utilizing dialkyl formamide alkylacetals in the steroid and non-steroid areas. In view thereof, the procedures of the present invention are totally unpredicted by the art. Nevertheless, a review of related reactions may be considered to be illuminating.

Parker and Kosley (the applicants herein) studied the reaction of certain alkynyl alcohols with dimethyl acetamide diethyl acetal (Tetrahedron Letters, 341 (1976) ) and found that in the case of tertiary propargyl alcohols in which the acetylene is terminal there are afforded products derived from dimethyl amino addition to the non-terminal carbon of the acetylene.

Buchi et al (JACS. 96 5563 (1974)) report the conversion of certain allylic alcohols to $\beta,\gamma$-unsaturated N,N-dimethylamides by treatment with N,N-dimethylformamideacetals. This work discusses the differentiation between reaction of the aforesaid N,N-dimethylformamideacetals with previously reported work involving N,N-dimethylacetamideacetals wherein gamma delta unsaturated amides are formed.

SUMMARY OF THE INVENTION

The present invention is directed to a process for converting certain 17-hydroxy-17-ethynyl steroids into the corresponding 17(20)-21 steroid aldehydes. In this procedure the starting material is a steroid which can be generally characterized as having the formula

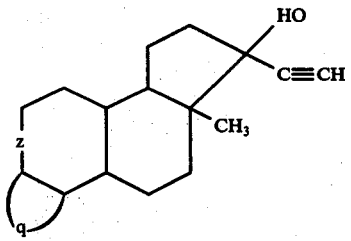

wherein—Z— is a carbon carbon single bond or a carbon carbon double bond and q is selected from the group consisting of

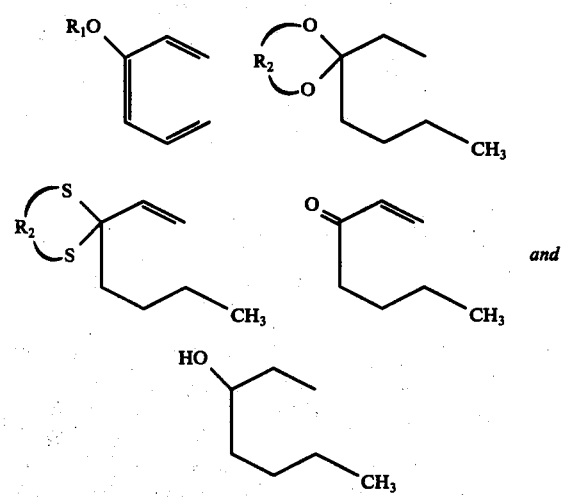

and provided that where
q is

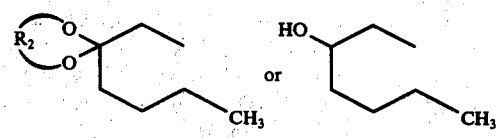

or z is a carbon carbon double bond and for the other values of $q$ z is a carbon carbon single bond with an excess of an N,N- diloweralkyl formamide diloweralkylacetal

wherein $R_3$ and $R_4$ are lower alkyl and may be the same or different and the term loweralkyl indicates an alkyl moiety of 1 to 5 carbon atoms to yield the corresponding dienamine of the formula

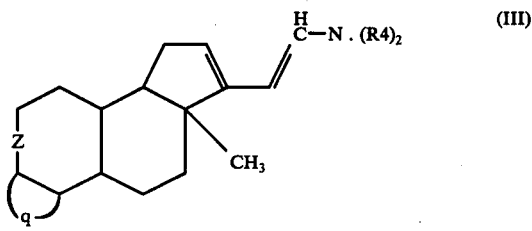

While the reaction is operative under a substantial range of reaction conditions, it has been found that certain factors substantially improve the overall yield and purity of the product. Namely, the presence of small amounts of carboxylic acid and small amounts of alkanol, suitably the alkanol having an alkyl group corresponding to that utilized in the loweralkyl moiety of diloweralkylacetal, have been found helpful.

It has also been found helpful to carry out the reaction at the reflux temperature of the acetal suitably 100°–120°.

The dienamine having the formula (III) which is formed in the first stage of this reaction is then isolated by removal of the volatile portions of the reaction mixture. No further purification is required.

The dienamine is then hydrolyzed to yield the aldehyde having the formula

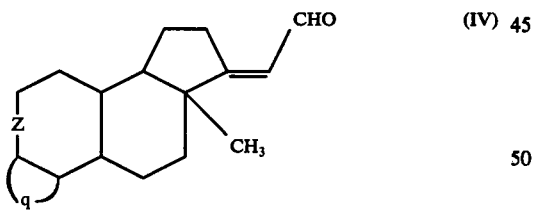

The conditions of hydrolysis are not critical provided that they are not so strong as to also remove any substituents protecting the 3 position steroid nucleus. Water, mild base, or mild acid are operative. However, the best results with respect to purity of product and efficiency of yield have been obtained by the use of moist silica gel, suitably by chromatographing the dienamine on a column of moist silica gel. The amount of moisture in the silica gel is not critical. However, it is known that if too high a proportion of water is contained in the silica gel particles the particles will swell, become sticky, and not permit the passage of organic solvents therethrough. Clearly the amount of water added to the silica gel should not approach this amount which is well known for those skilled in the art.

DESCRIPTION OF THE PREFERRED EMBODIMENT

The process of the present invention is directed to the formation of compounds having the formula IV as defined in the summary hereinabove. These compounds may be otherwise expressed in terms of a. the 3-ethers of 3-hydroxy-19-norpregna-1,3,5 (10)-trienes wherein the ether group may be alkoxy, suitably loweralkoxy of 1-5 carbon atoms for example, methoxy, ethoxy, propoxy, butoxy, or pentoxy; cycloalkoxy suitably lowercycloalkoxy of 3 to 7 carbon atoms in the cycloalkyl moiety, aryloxy suitably phenoxy, and aryl-loweralkoxy, suitably phenol loweralkoxy, wherein the alkoxy group is as defined hereinabove, b. The 3-alkylene ketals of 3 keto pregn-5-enes wherein the alkylene moiety is loweralkylene of 1 to 5 carbon atoms, suitably ethylene, c. The 3-alkylene thioketals of 3 keto pregn-4-enes wherein the alkylene is suitably loweralkylene of 1 to 5 carbon atoms preferably ethylene.

The starting materials in the present synthesis are the corresponding 17- ethynyl- 17-hydroxy analogs of the product suitably, but not critically, the 17 $\alpha$-ethynyl-17 $\beta$-hydroxy compounds. (I) The starting materials are taken up in a substantial excess of the desired N,N-diloweralkylformamide diloweralkylacetal (II) while any loweralkyl moiety of 1 to 5 carbon atoms may be employed and the two loweralkyl moieties may be the same or different.

These alkyl moieties may be for example, ethyl, methyl, butyl or pentyl. It has been found convenient to carry out the reaction using dimethylformamide diethylacetal. (II) While no additional substances are necessary for the reaction to be operative, nevertheless, it has been found that higher yields and better purities are obtained in the presence of a catalytic amount of a carboxylic acid and even better yields and purities are obtained in the further presence of a loweralkanol. The carboxylic acid may be any organic carboxylic acid suitably an alkanoic acid containing 1–10 carbon atoms. Suitably pivalic, n-propionic, n-butyric, iso-butyric or 2,2-dimethylbutyric acids may be used. It has been found that pivalic acid is especially suitable.

With respect to the alkanol any alkanol may be employed. However, it is preferred to utilize a loweralkanol suitably of 1–5 carbon atoms. Most suitably the alkanol corresponding to the alkyl moiety attached to the formamide group. Thus, in the preferred modification where N,N-dimethylformamide diethylacetal is employed, the alkanol is suitably ethanol. (II)

In the process of the reaction the ethynyl carbinol (I) is taken up in a substantial excess of the acetal. Excess amounts are not critical. However, it has been found suitable to utilize between 10 and 30, preferably about 20 equivalents, of acetal per mole of ethynyl carbinol. (I) It is especially preferred to carry out the reaction at the reflux temperature of the acetal, (II) heating at that temperature from between 1 to about 8, suitably from about 3 to about 5 hours and permitting the reaction mixture to cool to room temperature. In the most preferred embodiment there is employed between 1 and 5, suitably about 2 parts by weight of carboxylic acid per hundred parts by weight of the ethynyl carbinol (I). Further, there is also employed from between about ½ to about 3, suitably about 1 part by volume of the alkanol per 10 parts by volume of the acetal. (II)

Upon completion of the reaction the volatile constituents of the reaction mixture are removed suitably under reduced pressure to yield the dienamine (III) which may be utilized in the next stage of the reaction. Unless it is desired to isolate the dienamine (III) per se which is sensitive to deterioration in the presence of air and moisture, it is not necessary to remove all of the volatile constituents. Indeed such removal may be ignored where solvent volumes are small.

The dienamine (III) or the solution thereof, is then taken up in a suitable polar solvent suitably a solvent which is very slightly but not totally miscible with water, the criteria of the solvent being that it shall absorb sufficient water to permit hydrolysis of the dienamine (III) without carrying the dienamine (III) or the steroid aldehyde (IV) formed in the hydrolytic reaction into water solution, or on the other hand, throwing it out of solution. For this purpose halogenated solvents suitably halogenated hydrocarbon solvents such as chloroform have been found suitable.

Hydrolysis may be carried out by shaking the chloroform solution with aqueous acid or base. The latter is not especially recommended since chloroform and bases tend to form emulsions. It has been found that the most desirable way of obtaining clean and complete hydrolysis has been to contact the chloroform solution with silica gel. Preferably the silica gel has previously been shaken with water. The size of the silica gel mesh is not critical. However, 60 to 200 mesh has been found suitable. Furthermore, it has been found suitable to treat each 10 grams of gel with between 1 and 20 ml of water. 1 ml has been found especially suitable. The use of larger amounts of water will not interfere with the course of the hydrolysis. However, the silica gel will be caused to swell to such an extent that if the column method utilized below is employed for purification, the solvents may not pass therethrough.

In the preferred embodiment the silica gel is charged to a column in a suitable solvent, preferably in chloroform. The dimensions of the column utilized are not critical. However, it has been found suitable to utilize approximately 30 grams of silica gel to 500 mg of steroid ethynyl carbinol (I) originally utilized. This ratio can be varied by using substantially more or substantially less silica gel. However, this ratio has been found to be economical as a gel and gives excellent yields of high purity products.

A solution of the dienamine (III) in the minimum amount of chloroform is charged to the top of column and eluted with a further charge of chloroform. It has been found that approximately 3 to 5 column volumes of chloroform elute all of the steroid aldehyde (IV) formed.

Removal of the solvent under reduced pressure yields the steroid aldehyde. (IV) The steroid aldehyde may, if desired, be triturated with cold hydrocarbon solvent, suitably cold hexane, to provide the aldehyde (IV) in crystalline form. Very high purity material may be obtained by recrystallization from cyclohexane.

It should be noted that prior to trituration but after the hydrolytic chromatography, rechromatography is desirable. For example, it has also been found suitable to utilize a mixture of hexane and ethylacetate suitably a 9:1 (v/v) mixture of hexane and ethylacetate particularly for the chromatography of the thioketal embodiment of the present invention.

As stated heretofore the trans-loweralkoxy-19-norpregna-1,3,5(10,17(20)-tetra-en-21-als, suitably the 3-methoxy member of said group, have a known utility. The 3-alkylene ketals and thioketals are new compounds which may be readily converted into a known intermediate in the commercial synthesis of cortisone or hydrocortisone, namely trans-3-ketopregna-4,17(20)-dien 21-acetate, as may be the corresponding 3-keto-pregna-4,17(20)-dien and 3-hydroxy pregna-5,17(20)-dien-21-als.

In this procedure the ketal or the thioketal 21-aldehyde (IV (b) (c) ) is treated with a mile reducing agent suitably lithium aluminum hydride or sodium borohydride or the like to reduce the 21-aldehyde (IV) to the corresponding 21-alcohol which is then acetylated by conventional means to yeild the 3-ketal or -thioketal 21-acetate. Hydrolysis with mild acid, suitably dilute sulphuric acid, will remove the ketal group yielding the corresponding 3-keto pregna-4,17(20)-dien 21-acetate. Likewise hydrolysis with mild acid, suitably dilute sulfuric acid, in the presence of mercuric ion or treatment with methyl iodide inaqueous acetone in the presence of sodium carbonate will remove the thioketal group yielding the same 3-keto pregna 4,17(20)-diene-21-acetate. As stated heretofore, all of the three foregoing steps can be carried out by means well known to those skilled in the steriod art, Schnieder & Hanze, U.S. Pat. No. 2,796,823 (1956).

EXAMPLE I

The Preparation of Trans-3-Methoxy-19-Norpregna-1,3,5(10),17(20)-Tetraen-21-al.

A solution of 5 ml N,N-dimethylformamide diethylacetal (20 equivalents), 0.5 ml ethanol, 9 mg of pivalic acid and 0.505 g 17-α-ethynylestradiol-3-methyl ether was heated at 120° for 4 hours and allowed to cool to room temperature. The solution was dissolved in a minimum amount (3-5 ml/5 ml solution) of chloroform. The chloroform solution was placed on a column (dimensions not critical) packed with 60 g silica gel (60-200 mesh) which had been previously shaken with 6ml of water. The column was eluted with 200 ml of chloroform. Evaporation at 45° at 1 mm provided a white solid. Trituration with cold hexane provided 0.49 1 g (97.3%) of trans-3-methoxy-19-norpregna-1,3,5(10),17(20)-tetraen-21-al, m.p. (corrected) 166°-168°.

Recrystallization from cyclohexane afforded material with melting point 167°-169° (reported 170°-172°, W. R. Benn, *J. Org. Chem.*, 33,3117 (1969).

In accordance with the above procedure, but utilizing in place of N,N-dimethylformamide diethylacetal the corresponding dimethyl, dipropyl or dibutyl acetals there is obtained the same product.

In accordance with the foregoing procedures, but utilizing in place of ethanol, methanol with the dimethylacetal, propanol with the dipropylacetal and butanol with the dibutylacetal there is obtained the same product.

In accordance with the above procedures, but where, in place of pivalic acid there is utilized n-propionic, n-butyric, iso-butyric or 2,2-dimethylbutyric acid there is obtained the same product.

In accordance with the above procedures, but where in place of 17-alpha-ethynyl estradiol-3-methylether there is employed the corresponding ethyl, propyl, butyl benzyl, or phenyl ether there is obtained the corresponding trans-3-ethoxy-,propoxy-,butoxy-,benzyloxy-, and phenoxy-, 19-norpregna-1,3,5,(10),17(20)-tetraen-21-al.

EXAMPLE II

The preparation of trans-3-ketopregna-4,17(20)-dien-21-al-3-ethylenethioketal.

A solution of 3 ml N,N dimethylformamide diethylacetal (~20 equivalents), 0.3 ml ethanol, 6 mg. of pivalic acid and 0.313 g 17- α-ethynyltestosterone-3-ethylenethioketal was heated at 120° for 9 hours under nitrogen and allowed to cool to room temperature. The solution was dissolved in a minimum amount of chloroform (3–5 ml/5ml of solution). The chloroform solution was placed on a column (dimensions not critical) packed with 60 g silica gel (60–200 mesh) which had been previously shaken with 6ml of water. The column was eluted with 200 ml of chloroform. The chloroform was evaporated (50° at 30 mm) to provide 0.5 g of material which was dissolved in 10% ethyl acetate in hexane (v/v) and placed in a column (dimensions not critical) containing 60 g silica gel (60–200 mesh). The column was eluted with 1 × 100 ml 10% ethyl acetate in hexane (v/v), 1 × 100 ml 20% ethyl acetate in hexane and 1 × 100 ml 50% ethyl acetate in hexane. Evaporation of the third and fourth fractions followed by trituration with pentane provided 0.197 g (62.8%) of trans-3-keto-pregna-4,17(20)-diene-21-al-3-ethylene-thioketal.

EXAMPLE III

The preparation of trans-3-Ketopregna-5,17(20)-dien-21-al-3-ethyleneketal.

A solution of 5 ml N,N-dimethylformamide diethylactal (~ 20 equivalents), 0.5 ml ethanol, 10 ml pivalic acid, and 0.523 g 17 - α-ethynyltestosterone-3-ethyleneketal was heated at 120° for 4 hours under nitrogen and allowed to cool to room temperature. The solution was dissolved in a minimum amount of chloroform (3–5 ml/5 ml of solution). The chloroform solution was placed on a column (dimensions not critical) packed with 60 g silica gel (60–200 mesh) which had been previously shaken with 6 ml of water. The column was eluted with 200 ml of chloroform. The chloroform was evaporated (50° at 30 mm) and the residue dried at 1 mm at room temperature. Trituration with anhydrous ether provides 0.138 g (26.5%) of trans-3-ketopregna-5,17 (20)-dien-21-al-3-ethylene ketal.

In accordance with the above procedure but starting with 17α-ethynyl testosterone or 17α-ethynyl -3,17-dihydroxypregn-5-ene there is obtained trans-3-keto-pregna-4,17(20)-dien-21-al m.p. 142°–147° C IR 1670, 1610, 2720 - cm$^{-1}$;

NMR 9.91 (d J= 8H — CHO), 5.8 (m 2H C=CH), 1.25 (s 3H — CH$_3$ (C19) ), 0.95 (s 3H - CH$_3$ (C18) )

and trans-3-hydroxy pregna-5,17 (20)-dien-21-al
m.p. 174.5°–177° C
IR 1645, 3480 cm$^{-1}$
NMR 9.93 (d J=9, H, —CHO) 5.79 (d of t H J=8 J=3 C=CH — CHO) 5.38 (br.s C=CH (C6) ) 3.55 (br.s, H CH OH) 2.15 (H OH) 1.06 (s 3 H—CH$_3$(C19) ) 0.89 (s 3H—CH$_3$ (C18) ).

EXAMPLE IV

The preparation of trans-3-methoxy-21-dimethylamino-19-norpregna 1,3,5,(10), 16,20 pentaene.

A solution of 5 ml N,N-dimethylformamide diethylacetal (~20 equivalents), 0.5 ml ethanol, 9 mg of pivalic acid and 0.505 g 17 - α-ethynylestradiol-3-methyl ether is heated at 120° for 4 hours and allowed to cool to room temperature. The reaction mixture is heated on a water bath (ca 90° C) under reduced pressure (.1 mm rlg) for 30 mins. to remove all volatile materials, to yield the title product.

IR: 1638 cm$^{-1}$, no bands at 2240 (C≡CH), or 3480 (OH) cm$^{-1}$.

N.M.R. = 0.88 (s, 3H CH$_3$), 2.68 (s, 6H N,Me$_2$), 3.74 (s, 3H CH$_3$O), 4.78 (d, J=14, 1H NMe$_2$CH=CH), 5.32 (s, broad, 1H=CH), 6.56 (d, J=14, 1H NMe$_2$CH=CH), 6.64 (s, broad, 1H aryl H), 6.67 (d, broad, 1H aryl H) and 7.18 (d, aryl H)

In accordance with the above procedure but where in place of 17α-ethynyl estradiol 3-methyl ether there is utilized 17α-ethynyl testosterone 3-ethylene thioketal, there is obtained trans-3-keto-21-dimethylaminopregna-4,16,20-trien 3-ethylene thioketal N.M.R. = 0.88 (s, 3H CH$_3$), 1.06 (s, 3H CH$_3$) 2.68 (s, 6H NMe$_2$), 3.33 (s, 4H CH$_2$-s), 4.73 (d, J=14, 1H N.Me$_2$, CH=CH), 5.28 (m, 1H=CH conj. ring), 5.51 (s, broad, 1H=CH, unconj. ring) 6.50 (d, J=14, 1H NMe$_2$CH=CH).

In accordance with the above procedure but where in place of 17α-ethynyl estradiol 3-methylether there is utilized 17α-ethynyl testosterone 3-ethylene ketal, there is obtained trans-3-keto-21-dimethylaminopregna-5,16,20-triene 3-ethylene ketal.

EXAMPLE V cl Reduction of 21 aldehyde ketal (Method of Sperna Wieland and Arens, Rec. Trav. Chim. 79 1293 (1960) )

A solution of lithium aluminum hydride (0.57 g, 15 mmoles) in either (50 ml.) is added dropwise during 20 minutes to a solution of trans 3-keto pregna-5,17(20)-dien-21-al 3-ethylene ketal (4 g, 9.6 mmoles) in absolute ether (25 ml) cooled to −10°; care being taken that the temperature never exceeded 0°. When complete the mixture is stirred for a further hour at room temperature after which the excess lithium aluminum hydride was decomposed by adding wet ether. Just sufficient dilute sulfuric acid is then added to dissolve the precipitate and the ethereal solution was separated, washed successively with water (20 ml), 2% sodium carbonate solution (20 ml) and again with water (20 ml). After drying for 24 hours over sodium sulfate and evaporating off the ether under reduced pressure, the residue is recrystallized to yield trans-21-hydroxy-3-ketopregna-5,17(20)-dien 3-ethylene ketal.

In accordance with the above procedure but starting with trans-3-keto pregna 4,17(20)-dien-21-al 3-ethylene thioketal there is obtained trans-21 hydroxy-3keto pregna 4,17(20)-dien-3-ethylene thioketal.

EXAMPLE VI

Conversion of 21-hydroxy 3-ketal to 21 hydroxy 3 ketone (Method of Fetizon & Jurion Chem. Commun. 382, (1972)

A solution of 100 mg. (0.256 mmoles) of the ketal or thioketal of Example V in 1 ml of acetone containing 0.1 ml of water is heated under reflux with 177 mg. (1.25 mmoles) of methyl iodide and 150 mg. (1.4 mmoles) of sodium carbonate, until no starting material could be detected by tlc. The reaction mixture is filtered and partitioned between water and ether. The ether phase is washed with water, dried over magnesium sulfate, and concentrated. The product is recrystallized to yield 21-hydroxy-3-keto pregna-4,17(20)-diene in each instance.

I claim:

1. A process which comprises reacting a cyclopenta deca hydro(a)naphthalene of the formula

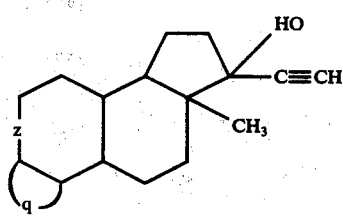

wherein —Z— is a carbon carbon single bond or a carbon carbon double bond and $q$ is selected from the group consisting of

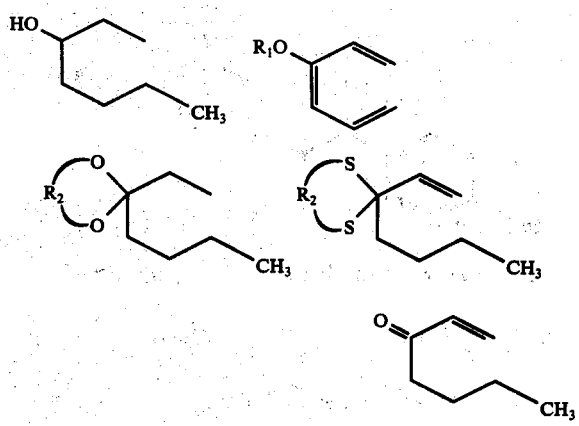

where $R_1$ is lower alkyl, phenyl or phenyl loweralkyl, $R_2$ is loweralkyl provided that where $q$ is

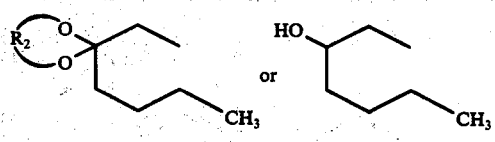

$z$ is a carbon carbon double bond and for the other values of $q$, $z$ is a carbon carbon single bond with an excess of a diloweralkyl formamide diloweralkylacetal, wherein the term loweralkyl indicates an alkyl moiety of 1 to 5 carbon atoms

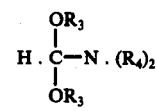

where $R_3$ and $R_4$ are loweralkyl and may be the same or different to yield the corresponding dienamine of the formula

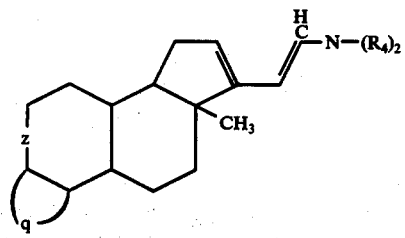

2. A process according to claim 1 which further comprises the step of hydrolyzing with a hydrolyzing agent selected from the group consisting of water, mild base and mild acid the dienamine produced in accordance with claim 1, to yield the corresponding alpha beta unsaturated aldehyde of the formula

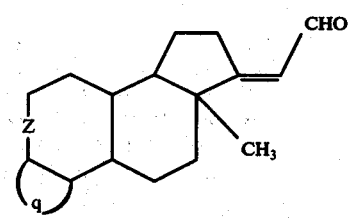

3. A process which comprises reacting a cyclopenta deca hydro(a)naphthalene of the formula

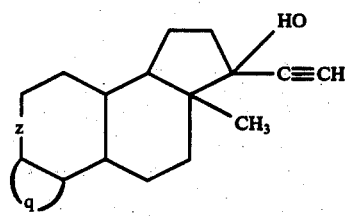

wherein —Z— is a carbon carbon single bond or a carbon carbon double bond and $q$ is selected from the group consisting of

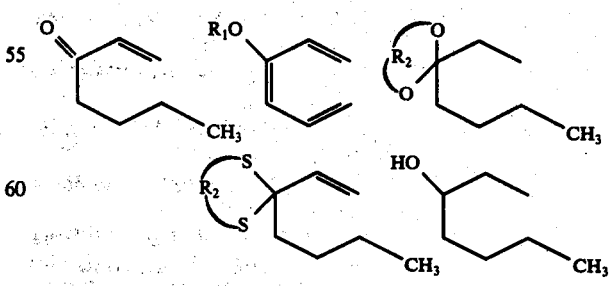

where $R_1$ is lower alkyl, phenyl or phenyl loweralkyl, $R_2$ is loweralkyl provided that where $q$ is

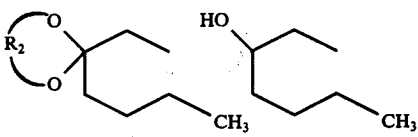

$z$ is a carbon carbon double bond and for the other values of $q$, $z$ is a carbon carbon single bond with an excess of a diloweralkyl formamide diloweralkylacetal wherein the term loweralkyl indicates an alkyl moiety of 1 to 5 carbon atoms

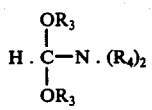

where $R_3$ and $R_4$ are loweralkyl and may be the same on different to yield the corresponding dienamine of the formula

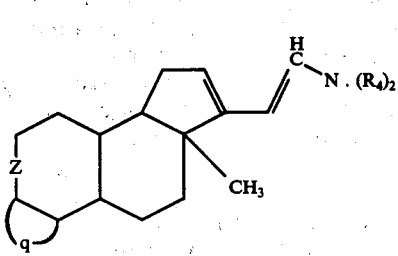

and hydrolyzing with a hydrolyzing agent selected from the group consisting of water, mild base and mild acid said dienamine to yield the corresponding alpha beta unsaturated aldehyde of the formula

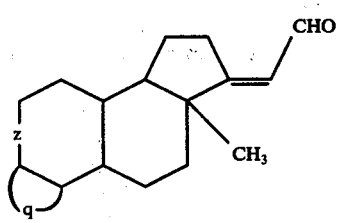

4. A process according to claim 3 wherein the dienamine forming reaction is carried out in the presence of a catalytic amount of a carboxylic acid.

5. The process according to claim 4 wherein the dienamine forming step is carried out in the additional presence of a catalytic amount of a lower alkanol containing 1 to 5 carbon atoms, and the carboxylic acid is an alkanoic acid of 1–10 carbon atoms.

6. A process according to claim 5 wherein the dienamine forming reaction is carried out at the reflux temperature of the diloweralkylformamide diloweralkylacetal.

7. A process according to claim 6 wherein the diloweralkylformamide diloweralkylacetal is dimethylformamide diethylacetal, the lower alkanol is ethanol, and the carboxylic acid is pivalic acid.

8. A process according to claim 3 wherein the dienamine is hydrolyzed by contact with water.

9. A process according to claim 8 wherein the dienamine is hydrolyzed by contact with silica gel containing water.

10. A process according to claim 9 wherein the silica gel contains between 5 and 20% by weight of water.

11. A process according to claim 10 which comprises the sequential steps of charging the dienamine to the top of a chromatographic column containing said silica gel and (b) eluting said column with a solvent of sufficient polarity to elute the alpha beta unsaturated aldehyde therefrom.

12. A process according to claim 11 comprising the additional step of removing the solvent from the eluate.

13. A dienamine of the formula

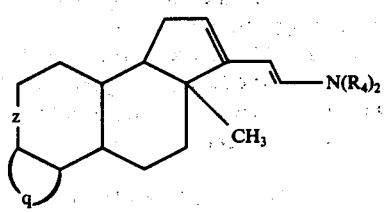

wherein $Z$, $q$ and $R_4$ are as defined in claim 1.

14. A dienamine of claim 13 having the formula:

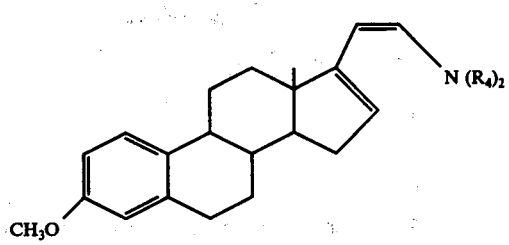

15. A dienamine of claim 14 having the formula:

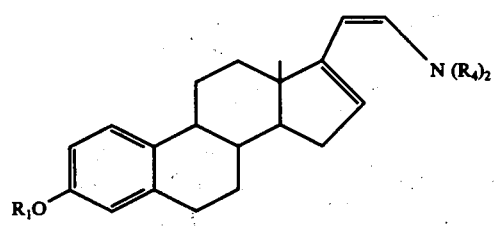

16. A dienamine of claim 13 having the formula:

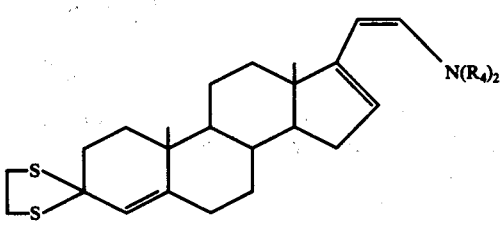

17. A dienamine of claim 13 having the formula:

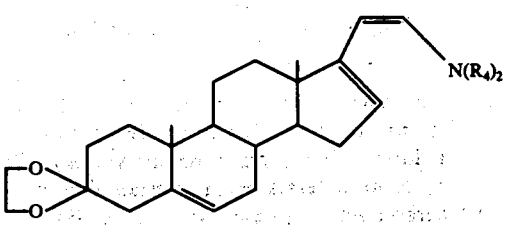

18. An alpha beta unsaturated aldehyde having the formula
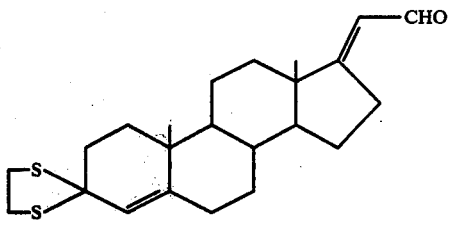
* * * * *